United States Patent
Kuepper et al.

(10) Patent No.: US 11,969,513 B2
(45) Date of Patent: Apr. 30, 2024

(54) IN-VEHICLE DECONTAMINATION

(71) Applicant: VOLKSWAGEN AKTIENGESELLSCHAFT, Wolfsburg (DE)

(72) Inventors: Philipp Nils Kuepper, Sacramento, CA (US); Jerramy Lee Gipson, Belmont, CA (US)

(73) Assignee: VOLKSWAGEN AKTIENGESELLSCHAFT, Wolfsburg (DE)

( * ) Notice: Subject to any disclaimer, the term of this patent is extended or adjusted under 35 U.S.C. 154(b) by 245 days.

(21) Appl. No.: 17/139,405

(22) Filed: Dec. 31, 2020

(65) Prior Publication Data
US 2022/0202969 A1  Jun. 30, 2022

(51) Int. Cl.
*A61L 2/10* (2006.01)

(52) U.S. Cl.
CPC ............ *A61L 2/10* (2013.01); *A61L 2202/14* (2013.01); *A61L 2202/16* (2013.01); *A61L 2202/20* (2013.01)

(58) Field of Classification Search
CPC .... A61L 2/10; A61L 2202/14; A61L 2202/11; A61L 2202/25; H05B 47/13; H05B 47/125
See application file for complete search history.

(56) References Cited

U.S. PATENT DOCUMENTS

| | | | |
|---|---|---|---|
| 2015/0273092 A1* | 10/2015 | Holub | B60Q 3/68 250/492.1 |
| 2015/0273093 A1* | 10/2015 | Holub | B60Q 3/68 250/492.1 |
| 2018/0193505 A1 | 7/2018 | Liao et al. | |
| 2019/0076558 A1 | 3/2019 | Zhang-Miske et al. | |
| 2019/0240363 A1 | 8/2019 | Kreiner et al. | |
| 2019/0298866 A1 | 10/2019 | Majdali et al. | |
| 2020/0306398 A1 | 10/2020 | Ruiter et al. | |

FOREIGN PATENT DOCUMENTS

| | | |
|---|---|---|
| WO | 2019190967 A1 | 10/2019 |
| WO | 2021195003 A1 | 9/2021 |
| WO | 2022066453 A1 | 3/2022 |

OTHER PUBLICATIONS

European Patent Office, Application No. 21210938.3, European Search Report dated May 19, 2022.
European Patent Office, Application No. 21210938.3, Office Action dated Mar. 13, 2023.

* cited by examiner

*Primary Examiner* — Sean E Conley
*Assistant Examiner* — Justin Hwang
(74) *Attorney, Agent, or Firm* — Shield Intellectual Property PC; Kirk D. Wong (57) ABSTRACT

A system and method for safe decontamination of a vehicle cabin while passengers can be present are disclosed that uses and/or has at least one data storage, at least one processor, at least one infrared ("IR") sensor, and at least one ultraviolet ("UV") emitter having a beam steering module. At least one contaminated area in the vehicle cabin is tracked using IR sensor data from the IR sensor. It is determined if there's a direct line of sight between the UV emitter and the at least one contaminated area. If so, UV emitter is activated to target the at least one contaminated area and blocking UV illumination on non-contaminated areas of the vehicle cabin and areas temporarily covered by a passenger.

19 Claims, 5 Drawing Sheets

IN-VEHICLE DECONTAMINATION

CROSS-REFERENCE TO RELATED APPLICATIONS

None.

FIELD

The present disclosure relates to methods, apparatuses, and systems for in-vehicle decontamination and, more particularly, to decontamination of a vehicle cabin using targeted UV light beams where passengers can be present in the vehicle.

BACKGROUND

In order to prevent contagions, e.g., COVID-19, from spreading, hygiene and sterilization are important aspects for mitigation strategies. Commonly shared spaces such as warehouses, workplaces, ride-sharing vehicles, taxis, and public transportation are potential hot spots for spreading contagions, even when people follow social distancing measures.

In particular for commercial vehicles (e.g., ride-sharing vehicles, public transportation buses and trains, and airplanes), there are many challenges to maintain a sanitized interior vehicle cabin, which need to be considered in a cost-benefit analysis. The factors that are weighed in such balancing include an amount of vehicle downtime for sanitization, cost of the sanitization, and reducing potential infection when transporting passengers in the vehicle.

Furthermore, the techniques for cleaning a vehicle have not changed in many decades. For instance, a common method is to manually wipe down a vehicle cabin with an antibacterial solution. Some vehicle operators have also placed a plastic barrier between passengers and a driver of a vehicle to add an additional layer of protection. Such techniques can be extremely time consuming to clean every inch of the vehicle cabin or install additional hardware, e.g., the plastic barrier. Even when all the appropriate steps are taken, such precautions may not fully work and only provide a false sense of security from contagions.

Thus, it's important to develop new methods, systems, and apparatuses for decontamination of a vehicle from contagions that are more efficient and may provide more security from transmission of contagions.

BRIEF DESCRIPTION OF THE FIGURES

The present disclosure is illustrated by way of example and not limitation in the figures of the accompanying drawings, in which like references indicate similar elements and in which.

DETAILED DESCRIPTION OF THE EMBODIMENTS

The figures and descriptions provided herein may have been simplified to illustrate aspects that are relevant for a clear understanding of the herein described devices, systems, and methods, while eliminating, for the purpose of clarity, other aspects that may be found in typical devices, systems, and methods. Those of ordinary skill in the art may recognize that other elements and/or operations may be desirable and/or necessary to implement the devices, systems, and methods described herein. Because such elements and operations are well known in the art, and because they do not facilitate a better understanding of the present disclosure, a discussion of such elements and operations may not be provided herein. However, the present disclosure is deemed to inherently include all such elements, variations, and modifications to the described aspects that would be known to those of ordinary skill in the art.

Figure 1:
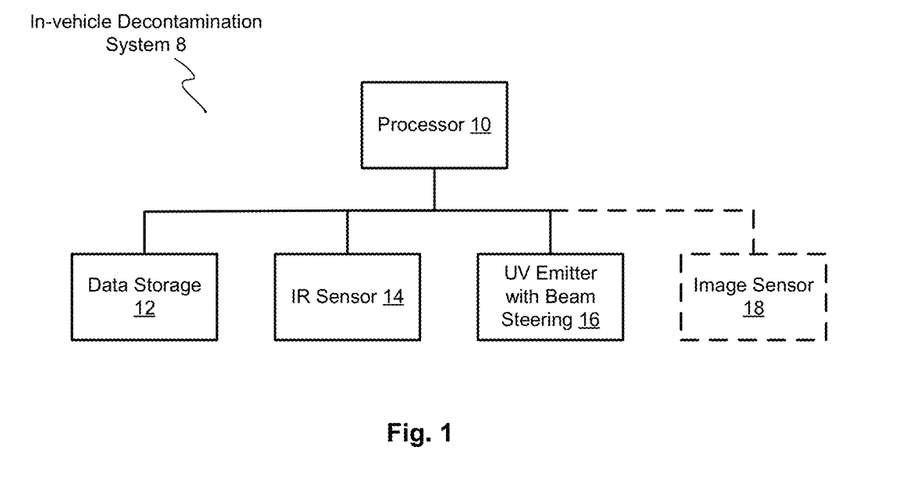
FIG. 1 is a block diagram in accordance with at least one embodiment of the present disclosure for an in-vehicle decontamination system.

FIG. 1 is a block diagram in accordance with at least one embodiment of the present disclosure for an in-vehicle decontamination system 8. The in-vehicle decontamination system 8 comprises a processor 10, a data storage 12, an infrared ("IR") sensor 14, an ultraviolet ("UV") emitter having a beam steering module 16, and, optionally, an image sensor 18. The processor 10 and data storage 12 can be onboard the respective vehicle and be communicatively coupled to the IR sensor 14, the UV emitter 16, and the image sensor 18.

The IR sensor 14, UV emitter 16, and the image sensor 18 are disposed within a vehicle cabin to sense areas with which a passenger (e.g., a vehicle driver or non-operating passenger) may interact or touch. For instance, in a sport utility vehicle ("SUV"), the IR sensor 14, UV emitter 16, and image sensor 18 can be collocated at a vehicle dome light, typically above the center console, on the roof of the SUV. From this vantage point, the IR sensor 14 can sense the movements of a passenger within the SUV. In addition, the IR sensor 14 can detect area(s) in the vehicle cabin which a passenger may have touched and/or breathed on based on the temperature profile of those detected area(s).

Areas of contamination of the vehicle are continuously tracked for targeted decontamination. The UV emitter 16 has a beam steering module to localize the UV light beam emission to the targeted areas to prevent passengers of the vehicle from being exposed to the UV light beams, which can be harmful to human tissue. Thus, the in-vehicle decontamination system 8 can actively illuminate targeted areas for decontamination while passengers are located inside the vehicle.

In at least one embodiment of the present disclosure, the image sensor 18 can be optionally included in the decontamination system 8 to track areas of contamination. The image sensor 18 can also perform a safety check to determine whether human tissue is blocking the targeted area in the vehicle cabin for decontamination. In another embodiment, the image sensor 18 can be an alternative for the IR sensor 14 and solely perform the tracking of contaminated areas.

It can be appreciated that other vehicle elements are inherently included to operate the in-vehicle decontamination system. For instance, the in-vehicle decontamination system 8 can be coupled to a power supply of the respective vehicle to power the various sensors 14 and 18, data storage 12, and processor 10. The power supply may be a source of energy that powers the engine/motor of the vehicle in full or in part and/or powers the electrical equipment of the vehicle.

In other embodiments, the processor 10 may be configured to store data in a local data storage of the vehicle (e.g., the data storage 12) and/or communicatively coupled to an external data storage that is remote from the vehicle.

In other embodiments, the processor 10 can be implemented by one or more processors. Those one or more processors may comprise one or more general-purpose processors and/or one or more special-purpose processors. To the extent the processor 10 includes more than one processor, such processors could work separately or in combination. The data storage 12, in turn, may comprise one or more volatile and/or one or more non-volatile storage components, such as optical, magnetic, and/or organic storage. The data storage 12 may contain computer program instructions (e.g., program logic) executable by the processor 10 to execute various functions (e.g., the methods disclosed herein).

The processor 10 may refer to data processing hardware, e.g., a CPU and/or GPU, TPU and/or NPU, and encompasses all kinds of apparatus, devices, and machines for processing data, including by way of example a programmable processor, a computer, multiple processors, computers, cloud computing, and/or embedded low-power devices (e.g., Nvidia Drive PX2). The processor 10 can also be, or further include, special purpose logic circuitry, e.g., an FPGA (field programmable gate array) or an ASIC (application-specific integrated circuit). The system can optionally include, in addition to hardware, code that creates an execution environment for computer programs, e.g., code that constitutes processor firmware, a protocol stack, a database management system, an operating system, or a combination of one or more of them. A computer program can also be used to emulate the respective computing system.

It can be appreciated that a computer program which may also be referred to or described as a program, (software, a software application, an app, a module, a software module, a script, or code) can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

In at least one embodiment, the IR sensor 14 can be implemented by one or more IR sensors. For more than one IR sensor, the IR sensors can be located along different areas within the vehicle cabin to provide additional accuracy. For instance, an IR sensor can be situated above each passenger sitting area in the vehicle to track a specific area in the vehicle.

In at least one embodiment, a long wave infrared ("LWIR") camera can be used as the IR sensor. The LWIR camera can provide additional functionality useful to track passengers, including pulse rate detection, respiration rate, characteristic heat profiles of tired versus awake people, etc. The LWIR camera allow for precise biometric analysis of passengers. UV cameras can also be used for this application, but may not provide as many secondary benefits as an LWIR camera.

The UV emitter with a beam steering module can be implemented by one or more UV emitters. The UV emitters can be located along different areas within the cabin to increase the amount of area in the vehicle cabin that can be illuminated by the UV emitters.

In addition, the optional image sensor 18 can be implemented by multiple image cameras located along different areas within the cabin to monitor the vehicle cabin. Similarly to the IR sensors, the image sensors can be situated above each passenger sitting area in the vehicle to track specific areas in the vehicle.

In at least one embodiment the IR sensors, UV emitters, and, optionally, image sensors can be collocated by grouping them together based on passenger area. For instance, a first grouping of an IR sensor, UV emitter, and, optionally, image sensor can be grouped and located on the roof above a left front passenger seat of the vehicle; a second grouping of an IR sensor, UV emitter, and image sensor can be grouped and located on the roof above a right front passenger seat of the vehicle; and a third grouping of an IR sensor, UV emitter, and image sensor can be grouped and located on the roof above rear passenger seats of the vehicle.

The first grouping can track movements of a passenger within the vicinity of the left front passenger seat and direct UV light beams to cabin areas in which that passenger may have contaminated. The second grouping can track movements of a passenger within the vicinity of the right front seat and direct the UV light beams to cabin areas in which that passenger may have contaminated. The third grouping can track movements of a passenger within the vicinity of the rear passenger seats of the vehicle and direct UV light beams to cabin areas in which the passenger may have contaminated.

Figure 2:
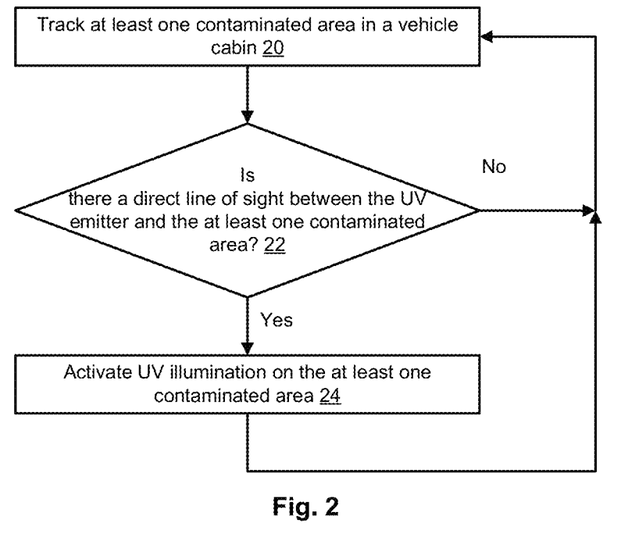
FIG. 2 is a flow chart in accordance with at least one embodiment of the present disclosure for an in-vehicle decontamination method.

FIG. 2 is a flow chart in accordance with at least one embodiment of the present disclosure for an in-vehicle decontamination method. A decontamination method can start by tracking at least one contaminated area in a vehicle cabin 20. Next, it's determined whether there is a direct line of sight between the UV emitter having a beam steering module 16 and the at least one contaminated area 22. If yes, the UV emitter is activated for UV illumination to target the at least one contaminated area 24. If no, the system continues tracking for contaminated areas 20 until it safe to decontaminate at least one of the contaminated areas by UV illumination 24.

The direct line of sight determination 22 also checks to make sure human tissue is not blocking UV illumination of the UV emitter on any identified contaminated areas. If so, then decontamination of the identified area is skipped and tracking 20 is continued. If human tissues is not blocking the identified contaminated area and there is a direct line of sight between the UV emitter and the identified contaminated area, then the identified contaminated area is targeted for UV illumination 24.

The in-vehicle decontamination method can be applied when the car is empty and when a passenger is present. When passengers are present, the in-vehicle decontamination method can operate in real-time and run while passengers are interacting with the car.

The decontamination method can be represented by computer program instructions that are stored on the data storage 12. The processor 10 is configured to execute the computer program instructions to perform tracking, determining, and activating steps 20, 22, and 24 discussed herein.

Figure 3:
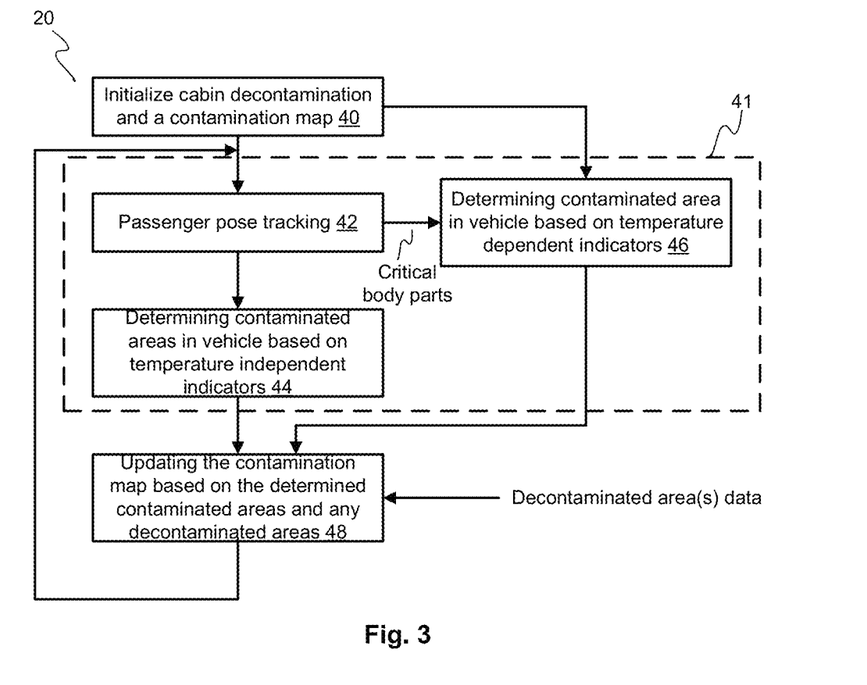
FIG. 3 is a flow chart in accordance with at least one embodiment of the present disclosure for tracking at least one contaminated area in a vehicle cabin.

FIG. 3 is a flow chart in accordance with at least one embodiment of the present disclosure for tracking at least one contaminated area in a vehicle cabin. The tracking step 20 further comprises several sub-steps. Cabin decontamination can be initialized 40. In at least one embodiment, the UV emitter may target all areas within its line of sight with UV illumination for decontamination. Such decontamination can take place when no one is sitting in the vehicle. Once the cabin area is initially decontaminated by the UV emitter, a contamination map can be initialized with a reference state in which all areas are identified as decontaminated.

In at least one other embodiment, the decontamination may be initialized to the last saved state of the decontamination map. The decontamination map can be saved to storage 12 so that the system can be reactivated and continue from its last saved state.

In another embodiment, the decontamination map be initialized with the reference state in which all areas are identified as decontaminated without having to first illuminate all areas within the line of sight of the UV emitter.

Once a passenger enters the vehicle, the IR sensor 14 and/or image sensor 18 can track the passenger within the vehicle. The passengers can be tracked 41 based on temperature independent indicators and temperature dependent indicators. A pose tracking algorithm can have a neural network and/or other algorithm to ingest the IR sensor data to generate a potential pose by the passenger 42. The potential pose is further used to determine likely areas in which the passenger may have touched within the vehicle 44. For instance, if the passenger pose is indicative of holding a steering wheel, the steering wheel is identified as a potentially contaminated area. The steering wheel can then be decontaminated by the UV emitter 16.

Additionally, the image sensor 18 can also be used to track temperature independent indicators. For instance, the image data can be used by a pose tracking algorithm to determine a pose for the passenger. With this information, likely areas which the passenger may have touched or otherwise interacted with within the vehicle can be determined based on that pose.

The IR sensor 14 senses infrared heat fluctuations within the layout of the vehicle cabin, which may be indicative of an area that was touched or otherwise interacted with by a passenger of the vehicle. The determined pose of the passenger is used to define areas within the vehicle to closer analyze 46. For instance, if a determined pose indicates that a passenger touched the center counsel (e.g., to adjust radio settings or adjust the temperature setting), the decontamination system can define the center counsel as an area of interest for further inspection based on the IR readings from the specific area. The temperature variations of the surface indicated by the IR readings may indicate areas in which a user has touched.

IR sensor technology (e.g., the IR sensor 14) has been shown to be able to detect human touches or human breaths based on the IR sensed data of the surfaces. The IR sensed data can detect imprints from surfaces affected by human interaction.

The IR sensor data and the pose information are used to determine if there are any areas indicative of an interaction with the passenger. If so, these areas can be identified as possible contaminated areas. The contamination map is updated 48 with the determined contaminated areas based on the temperature independent indicators and the temperature dependent indicators. It can be appreciated that the determined contaminated areas based on temperature independent indicators and the determined contaminated areas based on temperature dependent indicators can be aggregated or otherwise combined, and then used to update the contamination map. The aggregation can include summing all areas from both sets and then using the summed set for inclusion in the contamination map.

In other embodiments, various other methods to combine both sets of contaminated areas can be used as well in conjunction with the present disclosure. For instance, each contaminated area from each set can be weighted/prioritized based on indicator type, including whether the area is determined by temperature dependent indicators or by temperature independent indicators. Once weighted, the weighted sums from each set can be aggregated based on spatial coordinates to come up with a final contamination value assigned for a specific coordinate in the vehicle cabin. Coordinates that have assigned values above a predefined threshold are indicated as contaminated areas on the contamination map. Such weighting can be used and refined during the calibration phase of the system.

In addition, any areas in the vehicle cabin that have been decontaminated are updated 48 on the decontamination map. The IR sensed data from the IR sensor 14 and the UV illumination by the UV emitter 16 can be recorded with a corresponding timestamp of when each reading was sensed or when the UV illumination occurred. The timestamps can be used to determine whether decontamination occurred after a possible contamination by the passenger. If so, then the determined contaminated area is considered decontaminated and identified accordingly on the decontamination map. If not, the determined contaminated area is identified (or remains identified) as contaminated on the contamination map.

Figure 4:
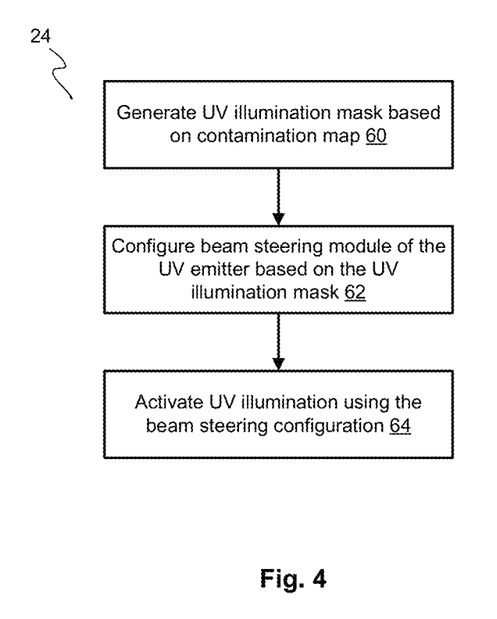
FIG. 4 is a flow chart in accordance with at least one embodiment of the present disclosure for activating UV illumination on at least one contaminated area in a vehicle cabin.

FIG. 4 is a flow chart in accordance with at least one embodiment of the present disclosure for activating UV illumination on at least one contaminated area in a vehicle cabin 24. Referring to FIG. 4, a UV illumination mask is generated based on the contamination map 60. The contamination map may have a coordinate system and resolution differences from the UV emitter with beam steering. Thus, data of the contamination map is translated to corresponding data of an UV illumination mask for the UV emitter to target the areas identified as contaminated. The UV illumination mask provides data to configure the beam steering module of the UV emitter 62. The UV emitter provides targeted UV illumination only on the identified contaminated areas of the vehicle cabin. The other areas that are not identified as contaminated are not illuminated by the UV emitter.

Next, the UV emitter is activated for UV illumination and directed at the contaminated areas by the beam steering module of the UV emitter 64. The beam steering module can be a galvanometric mirror, Micro-opto-electromechanical systems, optical phased array ("OPA"), vertical cavity surface emitting laser ("VCSEL") arrays, or other beam steering solutions.

A galvanometric mirror, also referred to as mechanical galvanometric or piezoelectric mirror, use mirrors on very precise actuators usually driven by high accuracy servomotors. The light coming from the source is guided to the mirror and deflected depending on the position of the mirror element. The mirror surface elements can be either oscillating or rotating. Typical maximum field of views for this kind of beam steering is about 80 degrees, while maintaining practical pointing precisions of up to 0.01. The motors are either actuated by providing digital or analog steering signals. To measure the exact angular position of the mirrors mounted to the shaft, galvanometers are equipped with an extremely precise position detector, either an analog detector (which may be optical or capacitive), or a digital encoder.

Galvanometric mirrors are commonly broken down by actuator type (moving magnet or moving coil) and type of position detector (capacitive, optical, or digital). The size of these mirrors can be quite large up to 10's of mm$^2$ and the mirror surface quality is generally very good (e.g., little deformities/aberrations from perfect plane), which is beneficial for maintaining high beam quality through steering. Also, the large surface area of the mirror effectively allows for a large receiving aperture of these systems in monostatic designs, which in turn enables good signal-to-noise-ratio ("SNR") on the receiver for long range applications. The scan can be adjusted on the fly (frame to frame) by giving different control parameters to the galvo-steering controller, which can enable situationally dependent FoV in terms of positioning and density.

A micro-(opto-) electromechanical systems use small mirrors of m2 to mm2 size that can be actuated to control tip and tilt (and piston), using various technologies including electrostatic, magnetic, thermal, and piezoelectric. If tip and tilt can be adjusted with just one mirror, it is considered a bidirectional, or 2D mirror, which can effectively scan the entire FoV. Bidirectional MEMS can be packaged in small units and beam quality can be maintained. Isolating the steering commands in two directions can be challenging, especially when high angular resolution is critical. Alternatively, two 1D mirrors can be used, which results in a more complex design, larger physical size, and often comes with trade-offs for beam quality. On the other hand, 1D approaches are more robust and promise longer lifespan. MEMS mirrors are categorized in two operating modes: Resonant and non-resonant operation.

An optical phased array ("OPA") is a solid-state device that enables beam steering by exploiting a fundamental property of light known as the Huygens-Fresnel principle. The underlying idea is that the direction of the coherent light can be modulated by introducing small time delays in individual emitters arranged in an array. By aligning the emitters' phases of several coherent light sources, the light interferes constructively or destructively in the far-field at certain angles, enabling efficient and very high precision beam steering. Phase delays are usually introduced by changing the refractive index of certain materials. This can be achieved through various approaches such as programming birefringence of nematic liquid crystals, using thermo-optic phase shifters where the delay for each path is changed via the thermal index change of a given material or by modulating the wavelength that propagates through a grating. The angular resolution of OPA based approaches can be very high depending on the number of individual emitters. The more emitters are used, the finer the beam can be steered, resulting in high angular resolution (with clearly defined primary lobes). The size and spacing between individual emitters determines the maximum field of view. Smaller individual emitters allow for a larger maximum FoV.

A large array of light sources, such as VCSEL arrays, can be used directly to illuminate the scene in discrete areas. The UV emitter has a beam steering module to direct the UV light beams (such as a UV VCSEL array used as a focal plane array (FPA)) to target areas within the cabin for illumination. A directed light source is used to illuminate the affected areas in a spatially constrained manner. This can be achieved by using technologies such as VCSEL arrays. VCSEL arrays are arrays of tiny laser diodes. By placing the array in the focal plane of a wide FoV lens, these lasers can be used as addressable light source. The addressable light source needs to be calibrated to the IR sensor (e.g., a LWIR camera). Once an accurate calibration is achieved, pixel locations in the LWIR image can be translated to activation of individual VCSEL arrays in the illuminator array.

It can be appreciated that other beam steering methods and apparatuses can be used in conjunction with the present disclosure. For simplicity, the main types of beam steering methods are discussed herein for a fulsome disclosure. However, the present disclosure is not meant to be limited to such main beam steering methods explicitly stated herein.

Furthermore, the UV illumination upon a targeted area can be predefined in terms of intensity and duration. The intensity can be determined based on a minimum ultraviolet intensity necessary to kill or otherwise destroy contagions. Likewise, the duration of the UV illumination can be based on a minimum amount of time needed to destroy contagions at a particular level intensity. The material of the vehicle cabin may also play an important factor in determining UV intensity and duration since some materials are more resistant to maintaining contagions on its surface than others. It can be appreciated that the current state of the art has studies defining such factors for UV germicidal irradiation.

Figure 5:
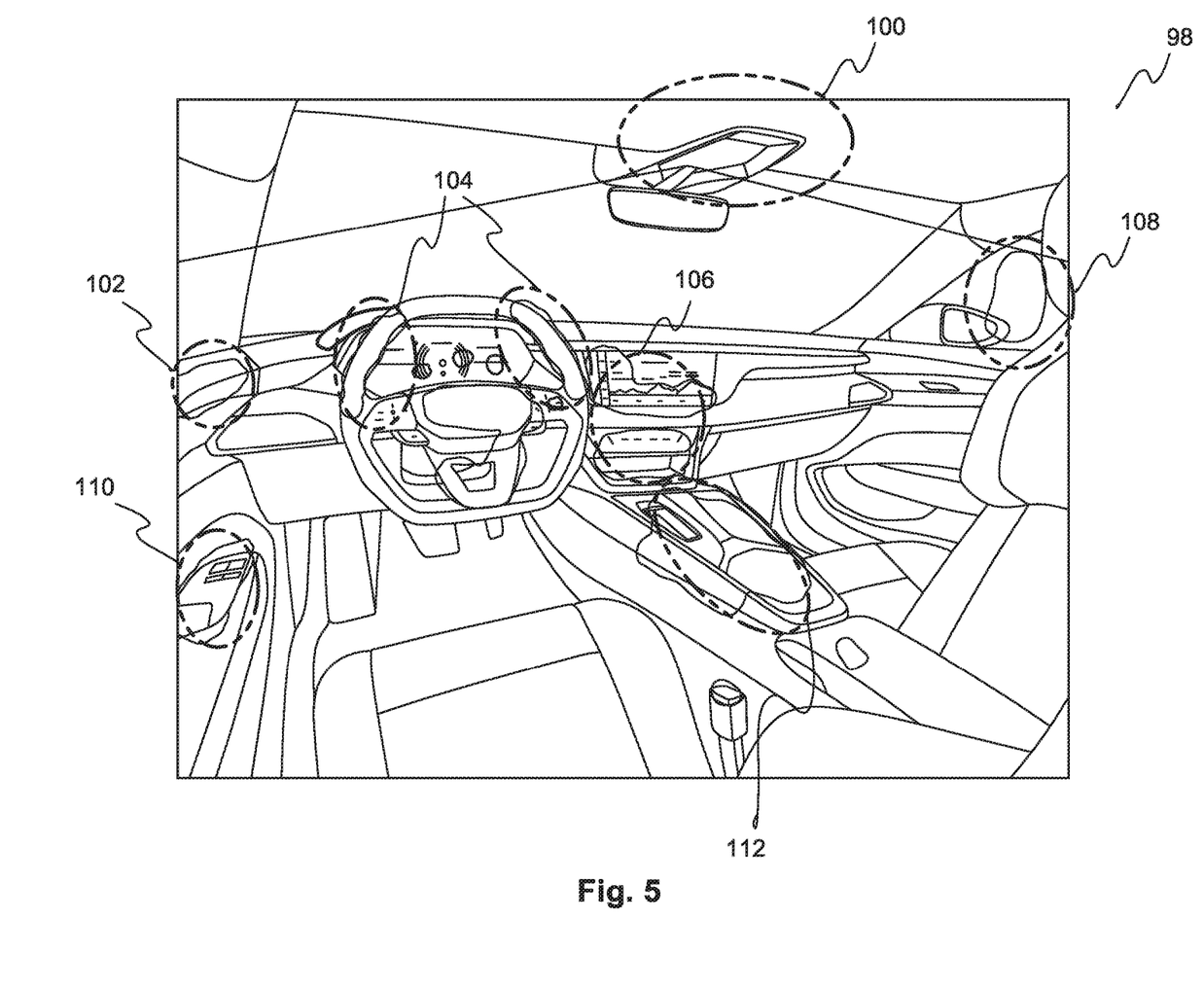
FIG. 5 illustrates a cabin area and a sample configuration for an in-vehicle decontamination system in accordance with at least one embodiment of the present disclosure.

FIG. 5 illustrates a cabin area and a sample configuration for an in-vehicle decontamination system in accordance with at least one embodiment of the present disclosure. In this embodiment, a LWIR (long wave infrared) camera and UV light sources are used for sanitation of a vehicle interior. A cabin-monitoring LWIR camera can also be used to monitor passengers, their physical contact with the interior of the car, including both tactile and a passenger's breath through indirect means.

Referring to FIG. 5, a decontamination system 100 is attached to the ceiling of a vehicle cabin 98. The decontamination system 100 has an LWIR camera with field of view ("FoV") that captures various areas occupied by front passengers of the vehicle. The LWIR camera can indicate surfaces which may have been touched by a passenger by detecting the residual heat pattern indicated by the IR emitted from those surfaces. For instance, cabin areas 102-112 are examples of where a passenger may touch within the car. A driver may hold the steering wheel 104, or rest his/her on the middle console 112 and upper door frame 102. The decontamination system 100 can detect these touches and target them from decontamination when the arms and hands are moved away from those locations.

Likewise, a user's breath can be detected by the LWIR camera to show a projected range of areas within the cabin which the droplets from the breath may end up on. Additionally, those droplets may also render a perceptible temperature profile on the surface relative to the surrounding area indicative of passenger breath droplets. Such areas can be identified as potential contaminated areas.

The LWIR image information is used to detect and track locations and objects touched or breathed on by passengers via a generated contamination map. UV illumination is applied on these locations to kill and/or shorten the lifetime of contagions at such locations and surface. The UV light source has a very defined beam profile to locally illuminate the affected areas. The defined beam profile allows for the decontamination system to be used in real time while passengers are within the vehicle. The decontamination system only directs the UV light source on targeted areas while avoiding illuminating passengers to avoid unnecessary UV light exposure.

The reason for this is that UV light is known to cause severe illness such as skin cancer and cataracts in human eyes. Absent these health concerns, UV light can be used to illuminate the entire cabin. By using directed beams, high intensities of UV light can be applied, which results in a significantly decreased lifetime of germs. When all passengers have left the car, UV light can be applied globally in the entire vehicle to sanitize the cabin and to reset the contamination map to a sterile origin.

The vehicle may have a user interface, e.g., a human-machine interface ("HMI"), and/or peripherals that are configured to allow a passenger to operate the decontamination system of the vehicle.

It can be appreciated that the disclosure can be combined with other ventilation and AC concepts in vehicles for sanitization. For instance, breathes from passengers can be routed away from the vehicle interior by sucking air near a passenger's head out of the vehicle via an air duct. For instance, this can be achieved through active air inlets in the headrest or console inlets in front of the passengers. Precise steering of air outlets and inlets can be used to isolate each passenger's breathable air. This can minimize the amount of air, and in turn germs, shared and breathed in by all passengers.

In at least one embodiment, a decontamination system of the present disclosure can be operated via a cloud connection to a backend server. Specifically, the subject matter described in this specification can be implemented in a computing system that includes a back-end component, e.g., as a data server, or that includes a middleware component, e.g., an application server, or that includes a front-end component, e.g., a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, e.g., a communication network. Examples of communication networks include wired and/or wireless local area networks ("LANs") and wired and/or wireless wide area networks ("WANs"), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

A vehicle communications system can be used to connect the vehicle to this backend controller. The vehicle communications system may be any system communicatively coupled (via wires or wirelessly) to one or more other vehicles, sensors, or other entities, either directly and/or via a communications network. The wireless communication system may include an antenna and a chipset for communicating with the other vehicles, sensors, servers, and/or other entities either directly or via a communications network. The chipset or wireless communication system in general may be arranged to communicate according to one or more types of wireless communication (e.g., protocols) such as BLUETOOTH, communication protocols described in IEEE 802.11 (including any IEEE 802.11 revisions), cellular technology (such as V2X, V2V, GSM, CDMA, UMTS, EV-DO, WiMAX, or LTE), ZIGBEE, dedicated short range communications (DSRC), and radio frequency identification ("RFID") communications, among other possibilities. The wireless communication system may take other forms as well.

While the functionality of the disclosed embodiments and the system components used to provide that functionality have been discussed with reference to specific terminology that denotes the function to be provided, it should be understood that, in implementation, the component functionality may be provided, at least in part, components present and known to be included in conventional transportation vehicles.

For example, as discussed above, disclosed embodiments use software for performing functionality to enable measurement and analysis of data, at least in part, using software code stored on one or more non-transitory computer readable mediums running on one or more processors in a transportation vehicle. Such software and processors may be combined to constitute at least one controller coupled to other components of the transportation vehicle to support and provide autonomous and/or assistive transportation vehicle functionality in conjunction with vehicle navigation systems, and multiple sensors. Such components may be coupled with the at least one controller for communication and control via a CAN bus of the transportation vehicle or other busses (e.g., Flexray).

It should further be understood that the presently disclosed embodiments may be implemented using dedicated or shared hardware included in a transportation vehicle. Therefore, components of the module may be used by other components of a transportation vehicle to provide vehicle functionality without departing from the scope of the present disclosure.

Terminology has been used herein for the purpose of describing particular illustrative embodiments only and is not intended to be limiting. The singular form of elements referred to above may be intended to include the plural forms, unless the context indicates otherwise. The method steps, processes, and operations described herein are not to be construed as necessarily requiring their performance in the particular order discussed or illustrated, unless specifically identified as an order of performance or a particular order is inherently necessary for embodiment to be operational. It is also to be understood that additional or alternative steps may be employed.

Disclosed embodiments include the methods described herein and their equivalents, non-transitory computer readable media programmed to carry out the methods and a computing system configured to carry out the methods. Further, included is a vehicle comprising components that include any of the methods, non-transitory computer readable media programmed to implement the instructions or carry out the methods, and systems to carry out the methods. The computing system, and any sub-computing systems, will typically include a machine-readable storage medium containing executable code; one or more processors; memory coupled to the one or more processors; an input device, and an output device connected to the one or more processors to execute the code. A machine-readable medium may include any mechanism for storing or transmitting information in a form readable by a machine, such as a computer processor. The information may be stored, for example, in volatile or non-volatile memory. Additionally, embodiment functionality may be implemented using embedded devices and online connection to cloud computing infrastructure available through radio connection (e.g., wireless communication) with such infrastructure.

It can be appreciated that embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively, or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

We claim:

1. A system, comprising:
   at least one infrared ("IR") sensor;
   at least one ultraviolet ("UV") emitter having a beam steering module, the UV emitter configured to emit targeted UV light to areas within a vehicle cabin;
   at least one data storage configured to store computer program instructions; and
   at least one processor communicatively coupled to the at least one data storage, the IR sensor, and the UV emitter,
   the at least one processor configured to execute the computer program instructions to perform:
   tracking at least one contaminated area, in the vehicle cabin using IR sensor data from the IR sensor;
   determining whether there is a direct line of sight between the UV emitter and the at least one contaminated area;
   generating a UV illumination mask by:
   activating UV illumination in the UV illumination mask to target the at least one contaminated area when there is the direct line of sight between the UV emitter and the at least one contaminated area; and
   deactivating UV illumination in the UV illumination mask to other areas in the vehicle cabin that are not identified as contaminated;
   configuring the beam steering module of the UV emitter based on the UV illumination mask; and
   activating the UV emitter for UV illumination by using the beam steering configuration to target the at least one contaminated area.

2. The system of claim 1 further comprising an image sensor communicatively coupled to the at least one processor, wherein the computer programming instructions further perform:
   tracking the at least one contaminated area using image data from the image sensor.

3. The system of claim 1 wherein the tracking at least one contaminated area further comprises:
   initializing cabin decontamination of the vehicle and a contamination map;
   determining the at least one contaminated area based on temperature independent indicators and temperature dependent indicators; and
   updating the contamination map based on the at east one contaminated area.

4. The system of claim 3 wherein the determining the at least one contaminated area further comprises:
   tracking passenger poses using a pose tracking algorithm; and
   correlating one or more areas of the vehicle cabin to the tracked passenger poses;
   wherein the one or more correlated areas are represented as contaminated areas in the contamination chap.

5. The system of claim 3 wherein the determining the at least one contaminated area further comprises:
   tracking one or more areas of the vehicle cabin having temperature variances indicative of an interaction with a passenger of the vehicle;
   wherein the one or more tracked areas are represented as contaminated areas in the contamination map.

6. The system of claim 3 wherein the generating the UV illumination mask further comprises:
   generating the UV illumination mask based on the contamination map.

7. The system of claim 1 where the computer programming instructions cause the at least one processor to further perform:
   updating a contamination map by setting the at least one contaminated area as a decontaminated area.

8. The system of claim 1 wherein the computer programming instructions cause the at least one processor to further perform:
   estimating a type of material representative of the at least one contaminated area: and
   determining a duration to activate the UV emitter on the at least one contaminated area based on the estimated type of material.

9. The system of claim 1 wherein the at least one IR sensor and the at least one UV emitter are collocated in a dome area at a front area in the vehicle cabin and near a rearview mirror.

10. The system of claim 1 wherein the beam steering module is a galvanometric mirror, a micro-opto-electromechanical system, an optical phased array, a vertical cavity surface emitting laser array, or combinations thereof.

11. A non-transitory computer readable medium encoded with instructions that when executed by at least one processor causes the processor to perform:
tracking at least one contaminated area in a vehicle cabin using 112 sensor data from an IR sensor;
determining whether there is a direct line of sight between a UV emitter and the at least one contaminated area;
generating a UV illumination mask by:
activating UV illumination in the UV illumination mask to target the at least one contaminated area when there is the direct line of sight between the UV emitter and the at least one contaminated area; and
deactivating UV illumination in the UV illumination mask to other areas in the vehicle cabin that are not identified as contaminated;
configuring the beam steering module of the UV emitter based on the UV illumination mask; and
activating the UV emitter for UV illumination by using the beam steering configuration to target the at least one contaminated area.

12. The non-transitory computer readable medium of claim 11, wherein the instructions that when executed by the at least one processor cause the processor to further perform:
tracking the at east one contaminated area using image data from an image sensor.

13. The non-transitory computer readable medium of claim 11, wherein the instructions that when executed by the at least one processor cause the processor to further perform:
initializing cabin decontamination of the vehicle and a contamination map;
determining the at least one contaminated area based on temperature independent indicators and temperature dependent indicators; and
updating the contamination map based on the at least one contaminated area.

14. The non-transitory computer readable medium of claim 13, wherein the determining the at least one contaminated area based on temperature independent indicators and temperature dependent indicators further comprises:
tracking passenger poses using a pose tracking algorithm; and
correlating one or more areas of the vehicle cabin to the tracked passenger poses;
wherein the one or more correlated areas are represented as contaminated areas in the contamination map.

15. A method, comprising:
tracking at least one contaminated area in a vehicle cabin using IR sensor data from an IR sensor;
determining whether there is a direct line of sight between a UV emitter and the at east one contaminated area;
generating a UV illumination mask by:
activating UV illumination in the UV illumination mask to target the at least one contaminated area when there is the direct line of sight between the UV emitter and the at least one contaminated area; and
deactivating UV illumination in the UV illumination mask to other areas in the vehicle cabin that are not identified as contaminated;
configuring the beam steering module of the UV emitter based on the UV illumination mask; and
activating the UV emitter for UV illumination by using e beam steering configuration to target the at least one contaminated area.

16. The method of claim 15, further comprising:
tracking the at least one contaminated area using image data from an image sensor.

17. The method of claim 15, further comprising:
initializing cabin decontamination of the vehicle and a contamination map;
determining the at least one contaminated area based on temperature independent indicators and temperature dependent indicators; and
updating the contamination map based on the at east one contaminated area.

18. The method of claim 17, wherein the determining the at least one contaminated area based on temperature independent indicators and temperature dependent indicators further comprises:
tracking passenger poses using a pose tracking algorithm; and
correlating one or more areas of the vehicle cabin to the tracked passenger poses;
wherein the one or more correlated areas are represented as contaminated areas in the contamination map.

19. The method of claim 17 wherein the determining the at least one contaminated area based on temperature independent indicators and temperature dependent indicators further comprises:
tracking one or more areas of the vehicle cabin having temperature variances indicative of an interaction with a passenger of the vehicle;
wherein the one or snore tracked areas are represented as contaminated areas in the contamination map.

* * * * *